(12) United States Patent
Alhumaid

(10) Patent No.: US 9,326,793 B2
(45) Date of Patent: May 3, 2016

(54) NEEDLE FOR PHYSICALLY SEPARATING AND PENETRATING THE PERICARDIUM

(71) Applicant: Fawaz Alhumaid, Lake Oswego, OR (US)

(72) Inventor: Fawaz Alhumaid, Lake Oswego, OR (US)

(*) Notice: Subject to any disclaimer, the term of this patent is extended or adjusted under 35 U.S.C. 154(b) by 205 days.

(21) Appl. No.: 13/943,542

(22) Filed: Jul. 16, 2013

(65) Prior Publication Data

US 2015/0025560 A1    Jan. 22, 2015

(51) Int. Cl.
| A61B 17/00 | (2006.01) |
| A61B 17/34 | (2006.01) |
| A61B 17/22 | (2006.01) |

(52) U.S. Cl.
CPC ......... *A61B 17/3496* (2013.01); *A61B 17/3468* (2013.01); *A61B 2017/00247* (2013.01); *A61B 2017/00398* (2013.01); *A61B 2017/00703* (2013.01); *A61B 2017/22039* (2013.01)

(58) Field of Classification Search
CPC ........... A61B 2017/00247; A61B 2018/00392; A61B 17/3403; A61B 17/3478; A61B 18/1477; A61B 2018/00642; A61N 1/0587; A61M 25/0084; A61M 2210/122
USPC .......... 606/185; 604/22, 164.01, 164.06, 262
See application file for complete search history.

(56) References Cited

U.S. PATENT DOCUMENTS

| 4,991,578 | A | 2/1991 | Cohen |
| 6,231,568 | B1 | 5/2001 | Loeb et al. |
| 6,442,415 | B1 | 8/2002 | Bis et al. |
| 6,666,844 | B1 | 12/2003 | Igo et al. |
| 6,692,458 | B2 | 2/2004 | Forman et al. |
| 2007/0161916 | A1* | 7/2007 | Zantos et al. ......... 600/517 |
| 2008/0208184 | A1* | 8/2008 | Davies ................ 606/34 |
| 2008/0294251 | A1 | 11/2008 | Annest et al. |
| 2010/0274129 | A1 | 10/2010 | Hooven |
| 2010/0331854 | A1 | 12/2010 | Greenberg et al. |
| 2012/0095434 | A1 | 4/2012 | Fung et al. |
| 2012/0316611 | A1* | 12/2012 | Armoundas et al. ......... 607/7 |

FOREIGN PATENT DOCUMENTS

WO    2012/048242    4/2012

* cited by examiner

*Primary Examiner* — Katherine M Shi
(74) *Attorney, Agent, or Firm* — Oblon, McClelland, Maier & Neustadt, L.L.P.

(57) ABSTRACT

A pericardial needle that punctures a pericardial membrane to attain access into a pericardial space of a heart by advancing a sharp tip until the sharp tip is adjacent to or in contact with a parietal pericardium of the heart such that the puncturing does not damage the heart muscle. The pericardial needle punctures the parietal pericardium when the heart muscle moves towards the pericardial needle, away from the pericardial needle, is at rest and/or is in synchronization with the systolic contraction period of the cardiac cycle of the heart. The synchronization may be provided based on a surface electrocardiogram, an arterial pressure, or a sensing pressure at the tip of the pericardial needle when the pericardial needle is adjacent into the parietal pericardium of the heart.

9 Claims, 16 Drawing Sheets

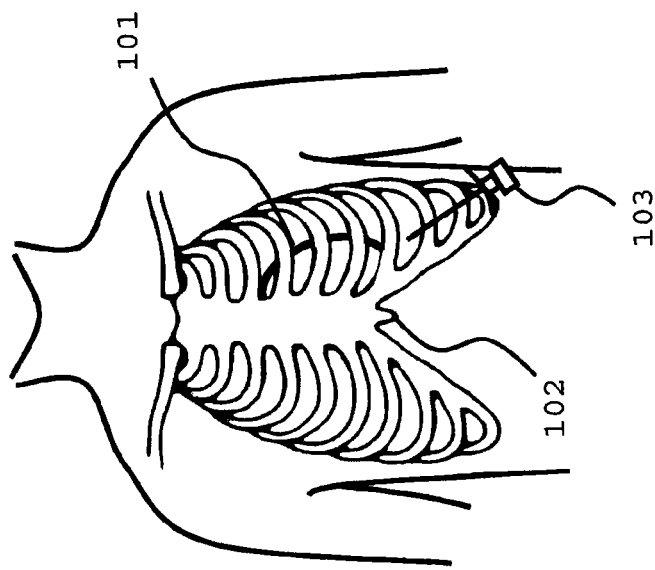
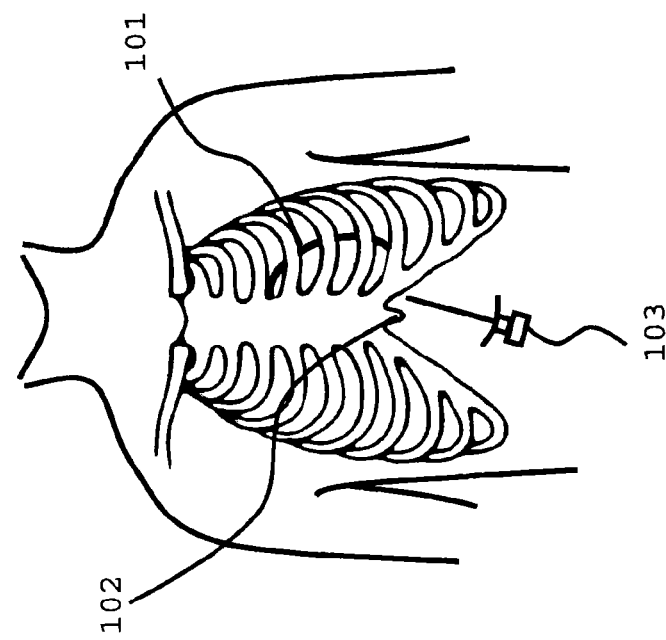
FIG. 1(a)
FIG. 1(b)

NEEDLE FOR PHYSICALLY SEPARATING AND PENETRATING THE PERICARDIUM

GRANT OF NON-EXCLUSIVE RIGHT

This application was prepared with financial support from the Saudi Arabian Cultural Mission (SACM), and in consideration therefore the present inventor has granted The Kingdom of Saudi Arabia a non-exclusive right to practice the present disclosure.

CROSS REFERENCE TO RELATED APPLICATIONS

The present application also contains subject matter related to that described in co-pending, commonly owned U.S. patent application Ser. No. 13/625,498, the contents of which being incorporated herein by reference in its entirety.

The present application contains subject matter related to that described in commonly owned U.S. patent application Ser. No. 14/224,245, titled "A Cautery Needle for Separating and/or Penetrating the Pericardium", incorporated herein by reference in its entirety.

BACKGROUND

Field of the Disclosure

The present disclosure relates to a pericardial needle that punctures the pericardial membrane. More specifically, the present disclosure relates to a pericardial needle that punctures the pericardial membrane by synchronizing needle advancement with cardiac muscle motion.

SUMMARY

The present disclosure relates to a pericardial needle that includes an outer needle, an inner needle disposed inside the outer needle, and a lumen disposed on an inner surface of the outer needle. The pericardial needle also includes a handle connected to the inner needle, and two springs (first and second springs) placed in opposite sides of the handle. The two springs are operable to provide force on the inner needle to retract and extend the inner needle from a tip of the outer needle. The handle and the two springs are located at an external end of the pericardial needle. The tip of the inner needle and the tip of the outer needle are located at a puncture end of the pericardial needle. The pericardial needle also includes a lock having a lock, a latch, an optional spring, and an electromagnet connected to a source of electricity and a controller. The lock is located between the handle and the puncture end of the pericardial needle. In operation, the inner needle is adapted to extend and retract in sequence with systole and diastole phases of heart contractions. Specifically, a first spring is compressed to engage the lock. The lock is activated in synchrony with the heart motion, releasing the inner needle at a time interval when the heart muscle contracts and moves away from the needle tip. The force generated by the compressed first spring advances the inner needle forward beyond the outer needle and puncture adjacent tissue, and briefly compressing a second spring beyond the baseline position. The second spring then expands pushing the inner needle back to a baseline position. Additionally, the inner needle may be retracted manually by applying the pressure on the handle.

BRIEF DESCRIPTION OF THE DRAWINGS

A more complete appreciation of the present application and many of the advantages thereof will be readily obtained as the same becomes better understood by reference to the following detailed description when considered in connection with the accompanying drawings, wherein:

FIGS. 1A and 1B are exemplary illustrations of two exemplary locations on the chest that may be used for the insertion of a pericardial needle to access the pericardial space of the heart;

DETAILED DESCRIPTION

As cardiac medical care advances, there is an increasing number of therapeutic procedures that require access into the pericardial space. Examples of such procedures include but are not limited to those needed for pacemakers, defibrillators, and ablation of certain arrhythmias. The pericardial space is a virtual space between the outside of the heart muscle and a thin layer of tissue that encases the heart muscle, called the parietal pericardium. The pericardial space contains a small amount of fluid, called the pericardial fluid.

The pericardial fluid is in constant contact with the heart muscle and the coronary arteries, and therefore, may be used, for example, to deliver drugs to the heart muscle and/or the coronary arteries. Since the pericardial fluid is of relatively low volume, such a method for drug delivery requires a relatively lower dose of drug.

Additionally, the pericardial fluid may be used to introduce an agent into the pericardial space, while localizing the agent to the area around the heart muscle. Such agent is contained within the pericardial fluid, without contaminating other tissue or parts. Also, due to the low turn over rate of the pericardial fluid, such agent is sustained over a relatively long period of time.

Figure 2:
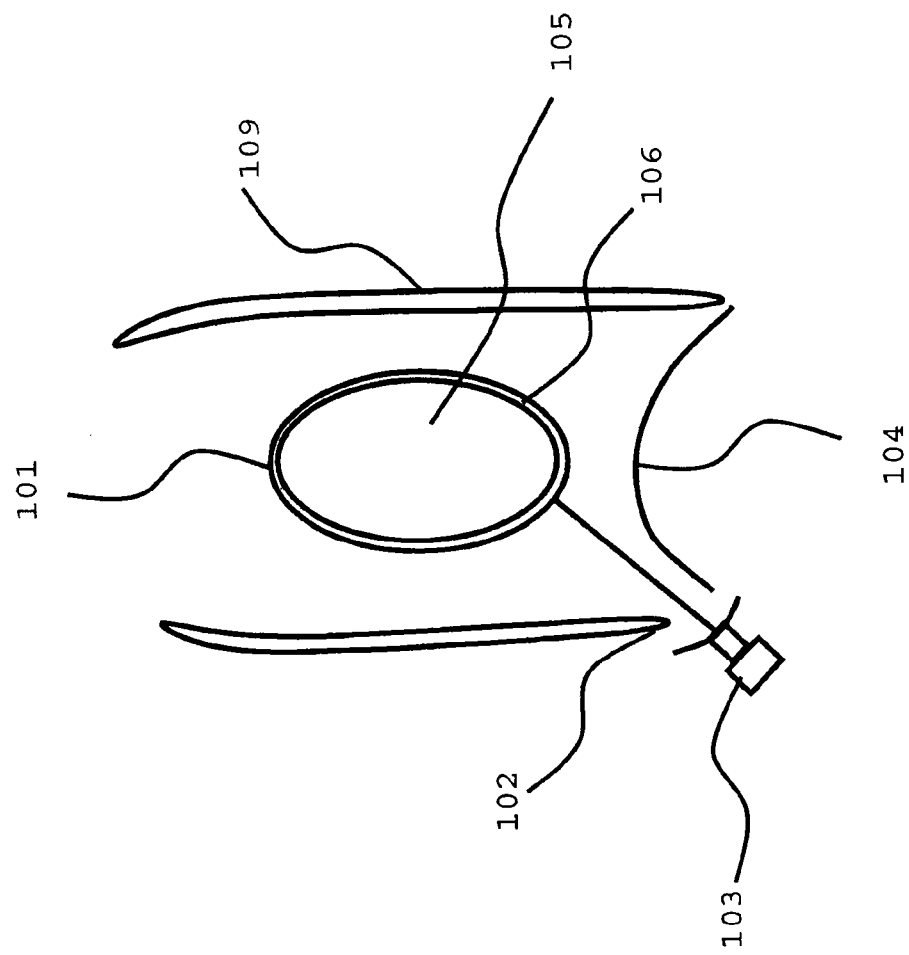
FIG. 2 is an exemplary side view illustration of an exemplary location on the chest that may be used for the insertion of a pericardial needle to access the pericardial space of the heart.

Conventionally, there are two commonly accepted locations on the chest that may be used for the insertion of a pericardial needle 103 to access the pericardial space 106: a) subxiphoid (FIGS. 1A and 2) and b) apical (FIG. 1B). Although the apical location corresponds to a lower risk of damaging extra-cardiac structures, as not many exist in the needle's path, it is generally avoided due to the presence of a major coronary artery (the left Anterior Decending Coronary Artery) in the area where the puncture occurs, and hence the associated risk of puncturing that artery and causing a heart attack. Access into the pericardial space 106 is attained with a blunt tip needle 103 adopted from the field of anesthesia, called the Tuohy needle. The Tuohy needle is an epidural introducer needle. To use the subxiphoid location to access the pericardial space 106 between the heart muscle 105 and the parietal pericardium 101, the needle 103 is carefully inserted between the Xiphoid process 102 and the diaphragm 104, as illustrated in FIG. 2, and advanced toward the heart muscle 105 in order to penetrate the parietal pericardium 101 without damaging or penetrating the heart muscle 101. Human back ribs 109 are also illustrated in FIG. 2 for clarity.

Multiple advancements of the needle 103, with gradual increase in pressure applied to the parietal pericardium 101 may be required until it is punctured. In order to determine if/when the parietal pericardium 101 is punctured, test injections of a contrast agent may be done following each advancement. Once the parietal pericardium 101 is punctured, the contrast agent can be seen filling the pericardial space 106. At this point, no additional punctures are required/performed.

With the exception of patients with pericardial effusion (patients with large amount of fluid collection in the pericardial space due to bleeding or other disease process), the process of accessing the pericardial space 106 is difficult with a relatively high complication rate due to the small space between the parietal pericardium 101 and the heart muscle 105 (few millimeters at most) and the continuous motion of the heart before, during, and after puncturing the parietal pericardium 101.

In some cases, the needle tip may penetrate the heart muscle 105, creating a blood leak from the inside of the heart into the pericardial space 106. Such blood leak can lead to tamponade and hypotension. In other cases, the needle tip may damage a coronary artery (arteries that supply the heart muscle with oxygen and nutrients), which can cause a heart attack. Such complications are life-threatening.

Other possible risks include damage to extra-cardiac structures that are present in the needle path. For example, the needle 103 may puncture the stomach, colon, liver, or diaphragm. It may also lacerate an artery causing significant bleeding. Such complications are serious, and potentially life-threatening.

Figure 3:
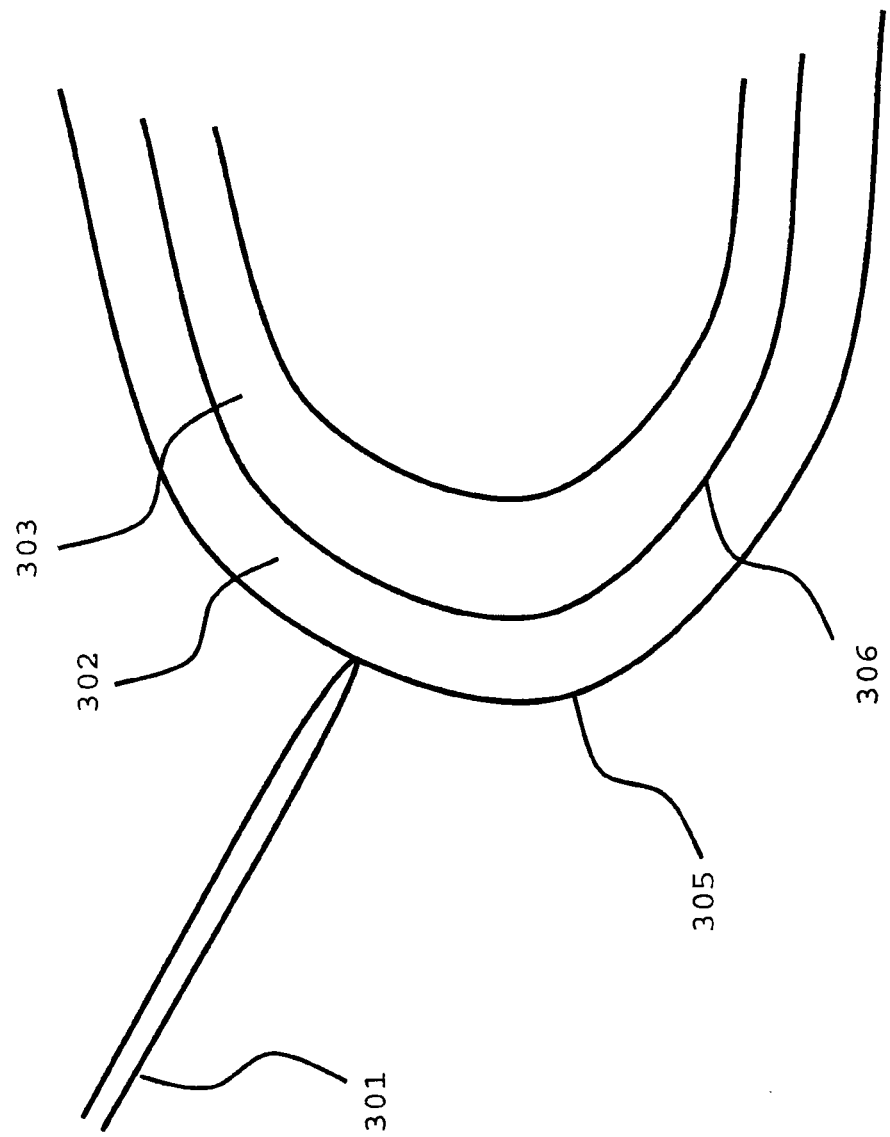
FIG. 3 is an exemplary cross-sectional illustrative view of accessing the pericardial space using a pericardial needle such that parietal pericardium, pericardial space, visceral pericardium, and myocardium are illustrated.

FIG. 3 is an illustrative view of a process for accessing the pericardial space 302 using a pericardial needle 301. Parietal pericardium 305, pericardial space 302, visceral pericardium 306, and myocardium 303 are illustrated in FIG. 3. The pericardial needle 301 must penetrate into the parietal pericardium 305 to access the pericardial space 302.

Figure 4:
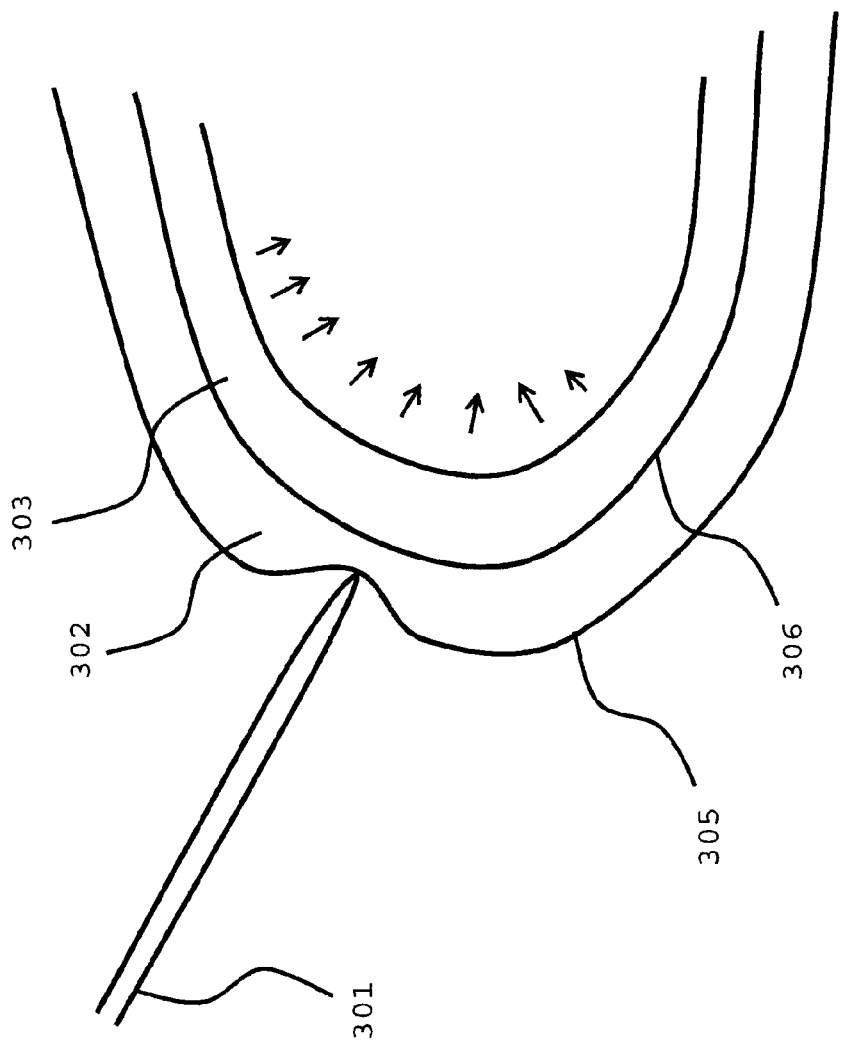
FIG. 4 is an exemplary cross-sectional illustrative view of a process for accessing the pericardial space when the heart is in systole.
Figure 5:
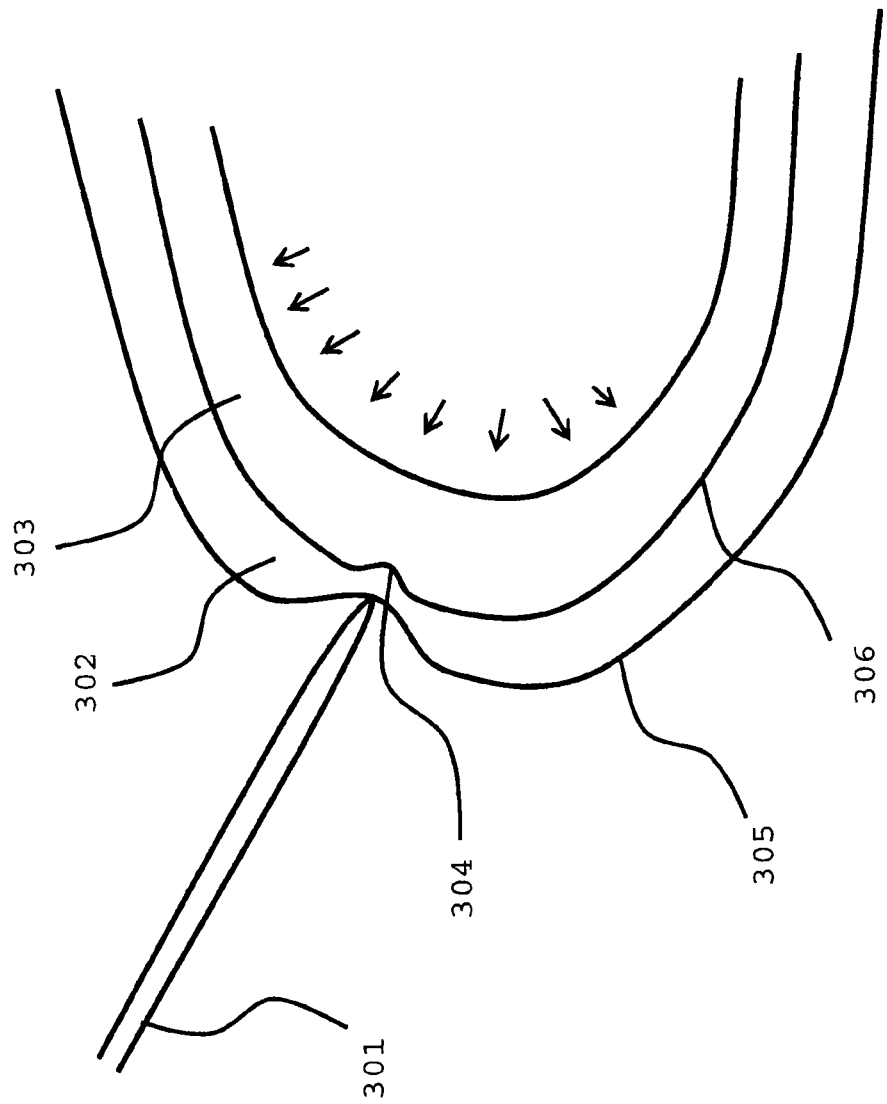
FIG. 5 is an exemplary cross-sectional illustrative view of a process for accessing the pericardial space when the heart is in diastole.

FIGS. 4 and 5 are illustrative views of a process of accessing the pericardial space 302 when the heart is in systole and diastole, respectively. The heart muscle or the myocardium 303 is in continuous motion. This motion is periodic and is called the cardiac cycle. The cardiac cycle is composed of two main phases called systole and diastole. Systole is the phase where the heart muscle 303 contracts, causing the heart to eject blood out of its inner cavities. Diastole is the relaxation phase during which the heart muscle 303 is relaxed and the heart chambers are filled with blood.

As the needle 301 advances towards the pericardial space 302, the motion of the heart muscle 303 has significant impact on the ability to achieve the goal of penetrating the parietal pericardium 305, without penetrating or damaging the adjacent moving heart muscle 303.

The inventor of the present disclosure identified that the risk of inadvertently penetrating the heart muscle 303 is significantly lower if the penetration of the parietal pericardium 305 is synchronized with the movement of the heart. This is due to the fact that the heart muscle 303 is moving away from the needle 301 during systole, and as shown in FIG. 4. Thus, the disclosed methods of the present disclosure take advantage of the motion of the heart muscle 303, and change this motion from a factor that adds to the risk of the procedure, to one that helps attain safer access to the pericardial space 302. That is, a motion of the needle may be synchronized with the motion of the heart.

The parietal pericardium 305 encases the heart muscle 303. The distance between the parietal pericardium 305 and the outer layer of the heart muscle 303 (the visceral pericardium 306) changes slightly as the heart muscle 303 moves. This change in the distance between the parietal pericardium 305 and the heart muscle 303 provides a time window of opportunity for a safer access to the pericardial space 302, when such access is synchronized with the movement of the heart muscle 303.

FIGS. 4 and 5 illustrate the indentation of the parietal pericardium 305 while the needle 301 is held in a fixed position. That is, the indentation of the parietal pericardium 305 is the same in systole and diastole, while on the heart muscle 303 there is no indentation in systole, but some minor indentation exists in the diastole.

According to an embodiment of the present disclosure, accessing the pericardial space 302 may be achieved by advancing the pericardial needle 301 through the parietal pericardium 305 in brief pulses, and synchronizing these pulses to systole where the heart muscle 303 contracts, thereby moving away from the needle 301. Alternatively, accessing the pericardial space 302 may be achieved by advancing the pericardial needle 301 through the parietal pericardium 305 when the heart muscle 303 expands (diastole) thereby moving towards the needle 301. This method can also be applied when the heart muscle is in rest in a static condition.

According to an embodiment of the present disclosure, accessing the pericardial space 302 may be achieved by inserting the pericardial needle 301 between the ribs at the left side of the chest. Although, important coronary arteries may exists in such location, the associated risk of inadvertently puncturing a coronary artery is reduced due to the synchronization of the needle advancement with the movement of the heart muscle 303, thereby making this location a viable option for using in the process of accessing the pericardial space 302.

In order to detect and synchronize with systole, visual, mechanical, electrical, or any similar measurement indicative and/or predictive of systole, diastole and/or the heart condition may be utilized. For example, according to an embodiment of the present disclosure, an echocardiogram may be used by a physician performing the process, to visually monitor the motion of the cardiac muscle.

Figure 6:
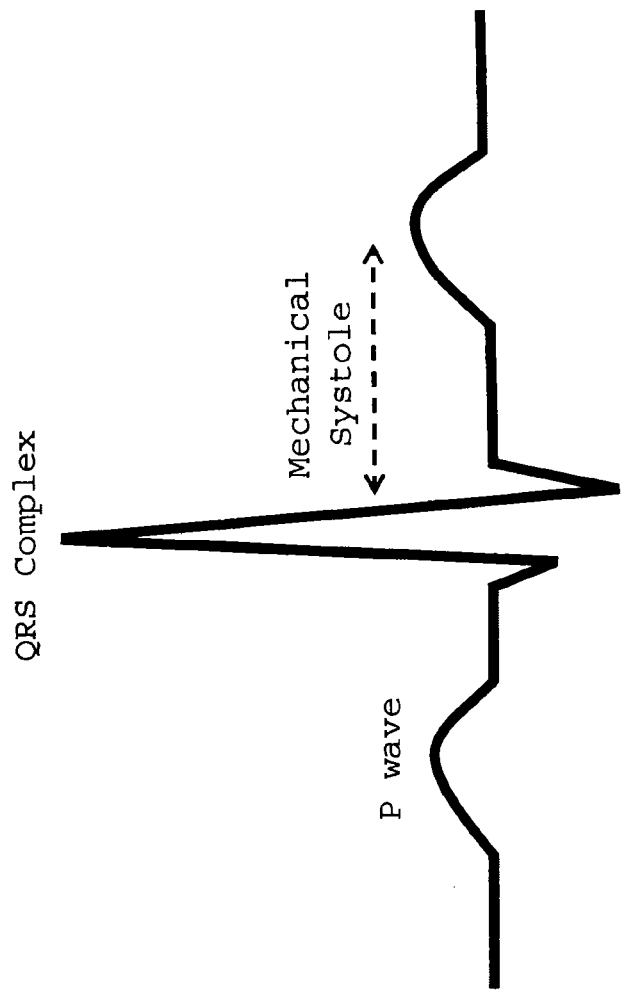
FIG. 6 is an exemplary graph of an electrocardiogram.

According to another embodiment of the present disclosure, an electrocardiogram (ECG) may be utilized to indicate the phase of the cardiac cycle, and synchronize with systole. FIG. 6 is a graph of an ECG, which is a recording of the electrical activity of the heart. A typical and exemplary ECG of the cardiac cycle (heart beat) consists of a P-wave, a QRS complex, and a T-wave. The P-wave reflects the atrial activation. The QRS complex reflects the ventricular activation, which is the electrical activity that causes the ventricular heart muscle 303 to contract. Accordingly, the actual systolic mechanical motion of the ventricles shortly follows the onset of the QRS complex shown in the ECG in FIG. 6.

Typically, mechanical systole starts approximately 30-40 msec after the QRS onset (e.g., beginning of the Q wave), and lasts for approximately 300-350 msec at resting heart rate in normal hearts. The duration of systole and the time between the onset of the QRS and the beginning of systole may be altered by, for example, the heart rate, age, gender, body mass index (BMI), and/or the presence of heart disease in a human patient.

According to an embodiment of the present disclosure, the needle 301 may be advanced preferably any time after the beginning, and before the end of systole. According to an embodiment, the needle may be advanced in a time window of, for example, 310 msec, starting at, for example, 40 msec after the QRS and ending at, for example, 350 msec after the QRS.

According to another embodiment of the present disclosure, the time window allowed for needle advancement may be adjusted based on one or more of many contributing factors including the heart rate, age, gender, and BMI of a patient, in addition to the presence and nature of underlying heart disease. Such adjustment may be in terms of a percentage of the time window. Such adjustment may be manually performed by the physician performing the process of puncturing the parietal pericardium 305, or may be automatically performed by a controller. Lab testing may be used to search for the best time interval during the cardiac cycle and/or during systole.

Figure 7:
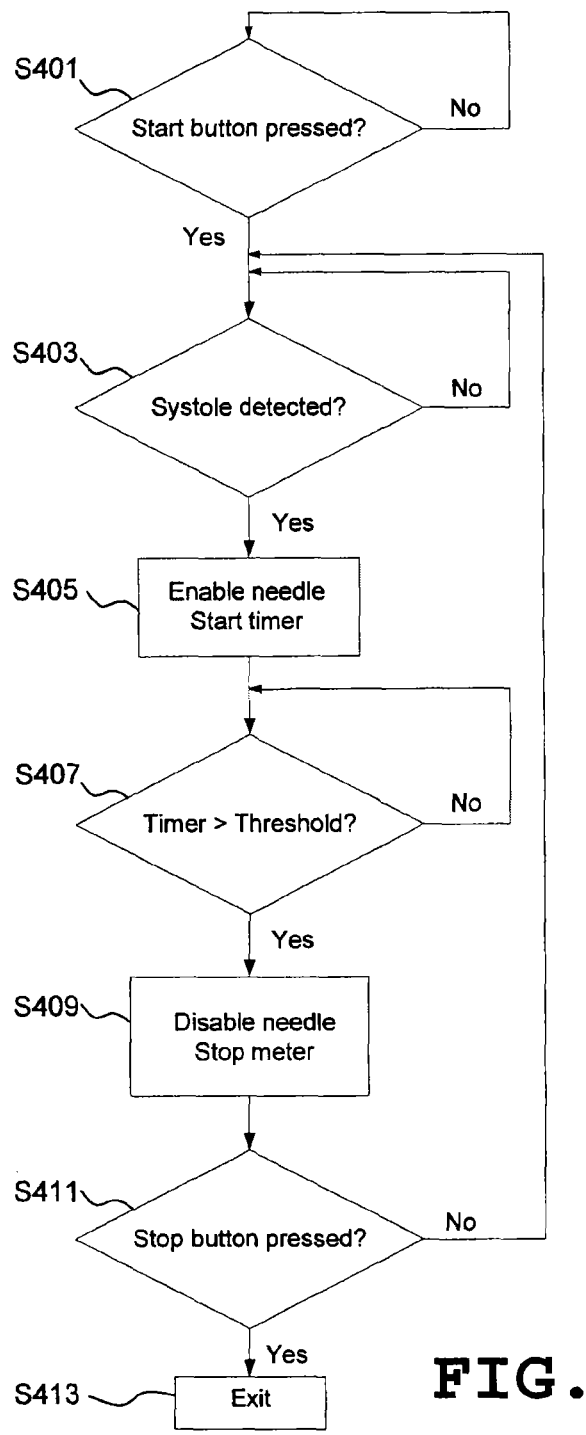
FIG. 7 is an exemplary flowchart for an embodiment of a method for synchronizing the process of accessing the pericardial space with the heart's systole using a pericardial needle.

FIG. 7 is a flowchart for an exemplary embodiment of a method for synchronizing the process of accessing the pericardial space 302 with the heart's systole using different embodiments of the pericardial needles 103, 301, 650, and/or 660 as disclosed in this application. In step S401, the process determines whether an instruction for initiation of the process has been given. For example, a start button may be pressed by a physician, indicating the initiation of the process of accessing the pericardial space 302. If no indication of initiation has been detected, the process loops back to step S401. Otherwise, the process proceeds to step S403.

In step S403, the process checks if systole is detected. Detection of systole may be according to visual, mechanical, electrical, or any other measurement indicative of systole. If systole is not detected, the process loops back to step S403. Otherwise, the process proceeds to step S405.

In step S405, the needle 301 is enabled and a timer is started. According to an embodiment, a cautery needle, previously held in a disabled state, may be enabled in step S405, such that the cautery needle punctures the parietal pericardium 305 when cautery is enabled. According to another embodiment, a needle blade, previously held in a secured state, may be released in step S405, such that the needle blade punctures the parietal pericardium 305 when released. According to another embodiment, a laser needle, previously held in an inactive state, may be activated in step S405, such that the laser needle punctures the parietal pericardium 305 when activated.

In step S407, the process checks if the timer has exceeded a predetermined threshold. The predetermined threshold may be set according to an estimate of the duration of systole from previous measurements. If the timer has not exceeded a predetermined threshold, the process loops back to step S407. Otherwise, the process proceeds to step S409.

In step S409, the needle 301 is disabled and the timer is stopped. According to an embodiment, a cautery needle is disabled in step S409, such that cautery is no longer deliverable, so that the needle does not punctures the parietal pericardium 305 when disabled. According to another embodiment, a needle blade is secured in step S409, such that the needle blade does not puncture the parietal pericardium 305 when secured. According to another embodiment, a laser needle is de-activated in step S409, such that the laser needle does not puncture the parietal pericardium 1305 when de-activated.

In step S411, the process checks if an instruction to stop needle advancement and/or stop the process has been received. For example, a stop button may be pressed by a physician, indicating the success and/or termination of the process of accessing the pericardial space 302. If the process has not been interrupted, the process loops back to step S403. Otherwise, the process exits in step S413.

Multiple advancement toward the parietal pericardium 305 may be required in order to successfully puncture the pericardial membrane. A physician may determine the success of puncturing the parietal pericardium 305 by monitoring the operation and looking for the indication that a test contrast agent injection flows into the pericardial space 302 as observed under fluoroscopy imaging. As previously mentioned, detection of systole may be according to visual, mechanical, electrical, or any other measurement indicative of systole.

Figure 8:
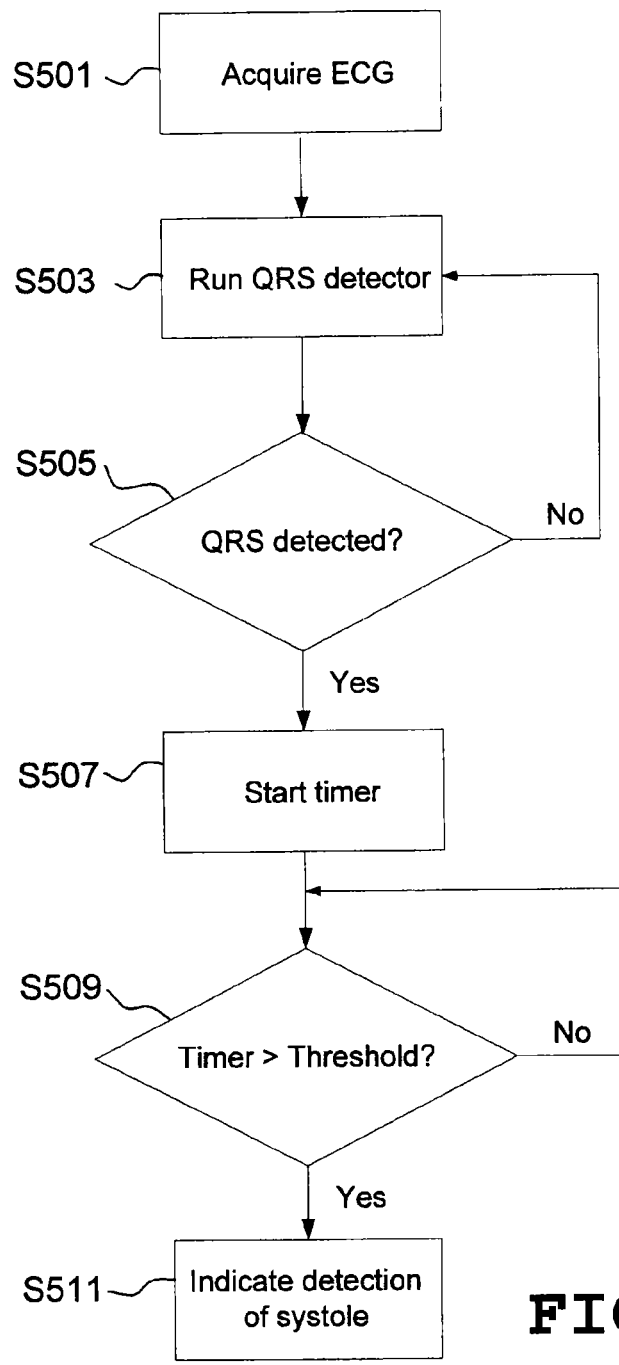
FIG. 8 is an exemplary flowchart for an embodiment of a method for detecting systole based on an electrocardiogram.

FIG. 8 is a flowchart for an embodiment of a method for detecting systole based on the ECG. In step S501, ECG is acquired. According to an embodiment, ECG may be acquired according to a conventional method, for example, via ECG electrodes, followed by ECG instrumentation and signal processing. According to another embodiment, acquisition of ECG may be performed according to conventional ECG electrodes, followed by, for example, ECG instrumentation and signal processing, and wireless transmission of the ECG signals to a controller. According to an embodiment, acquisition of ECG may be according to conventional ECG electrodes, followed by, for example, ECG instrumentation and signal processing, and fiber optic transmission of the ECG signals to a controller.

In step S503, a QRS detector is run. According to an embodiment, detection of QRS may be according to a conventional method of slope detection. According to another embodiment, detection of QRS may be according to an envelope or template detection. The envelope or template detection may be according to a previously acquired QRS, or according to a standard QRS profile or template. The standard QRS profile or template may be adjustable according to one or more of an age, gender, BMI, or heart rate of a human patient.

According to another embodiment, detection of QRS may be according to an extremum detection, such as an R-wave peak detection, a Q-wave minimum detection, or an S-wave minimum detection. Alternatively, detection of QRS may include detection of a sequence of extremums, e.g., a Q-wave minimum followed by an R-wave peak, or an R-wave peak followed by an S-wave minimum.

Detection of QRS may be performed in real-time, and with tolerable delay, such that the detected QRS corresponds to the mechanical activity of the heart in real-time. The tolerable delay between the onset of the QRS complex and the detection of the QRS complex may depend on the duration of systole, and/or the time period between the onset of the QRS complex and systole.

In step S505, the process checks if QRS is detected. If QRS is not detected, the process loops back to step S505. Otherwise, the process proceeds to step S507.

In step S507, a timer is started to measure the time elapsed since the detection of QRS.

In step S509, the process checks if the timer has exceeded a predetermined threshold. The predetermined threshold may be set according to an estimate of the duration of time between the detection of QRS and systole. If the timer has not exceeded the predetermined threshold, the process loops back to step S509. Otherwise, the process proceeds to step S511.

According to an embodiment, the predetermined threshold may be adjustable according to one or more of an age, gender, BMI, presence of underlying heart disease, or heart rate of a human patient.

In step S511, detection of systole is indicated. Alternatively, other similar methods may be used to indicate systole. According to an embodiment of the present disclosure, a pressure measurement may be used to synchronize the process of accessing the pericardial space 302 with systole. The pressure measurement may be performed at the tip of the needle 301. Alternatively, arterial pressure wave, through an arterial line, or pulse oximetery wave (Plethysmograph) may be used.

The arterial blood pressure indicative of systole may be determined by the measurement of the arterial blood pressure before the process of puncturing the parietal pericardium, and adjusting the expected arterial blood pressure during systole either manually or automatically. As the arterial blood pressure is subject to variation, such measurement may be monitored continuously, updated continually or from time to time, for example, 1, 10, 100, 500 micro seconds, or 1, 10, 100, 500 milliseconds, during the process of puncturing the parietal pericardium.

Figure 9:
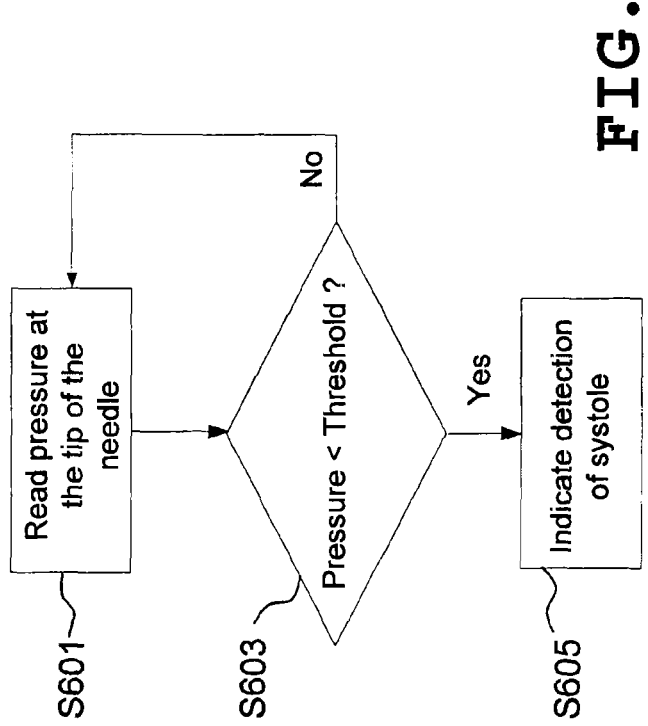
FIG. 9 is an exemplary flowchart for an embodiment of a method for detecting systole based on a pressure measurement at the tip of a pericardial needle.

FIG. 9 is a flowchart for an embodiment of a method for detecting systole based on a pressure measurement at the tip of the needle 301. In step S601, a pressure measurement is made at the tip of the needle 301. In step S603, the process checks if pressure has fallen below a predetermined threshold. The predetermined threshold may be set according to an estimate of the pressure expected at the tip of the needle 301 during systole. If the pressure has not fallen below the predetermined threshold, the process loops back to step S603. Otherwise, the process proceeds to step S605. The predetermined threshold may be adjustable according to one or more of an age, gender, BMI, or heart rate of a human patient. In step S605, detection of systole is indicated.

Figure 10:
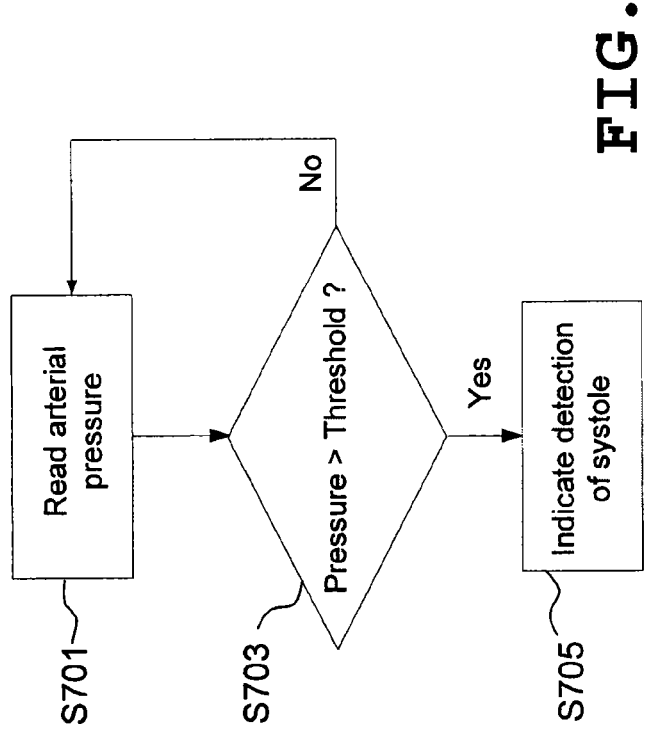
FIG. 10 is an exemplary flowchart for an embodiment of a method for detecting systole based on arterial pressure measurement.

FIG. 10 is a flowchart for an embodiment of a method for detecting systole based on arterial pressure measurement. In step S701, an arterial pressure wave is detected. The detection of the arterial pressure wave may be through an arterial line, or pulse oximetery wave (Plethysmograph). In step S703, the process checks if the arterial pressure has exceeded a predetermined threshold. The predetermined threshold may be set according to an estimate of the arterial pressure during systole. If the arterial pressure has not exceeded a predetermined threshold, the process loops back to step S703. Otherwise, the process proceeds to step S705. The predetermined threshold may be adjustable according to one or more of an age, gender, BMI, presence of underlying heart disease, or heart rate of a human patient. In step S705, detection of systole is indicated.

Figure 11:
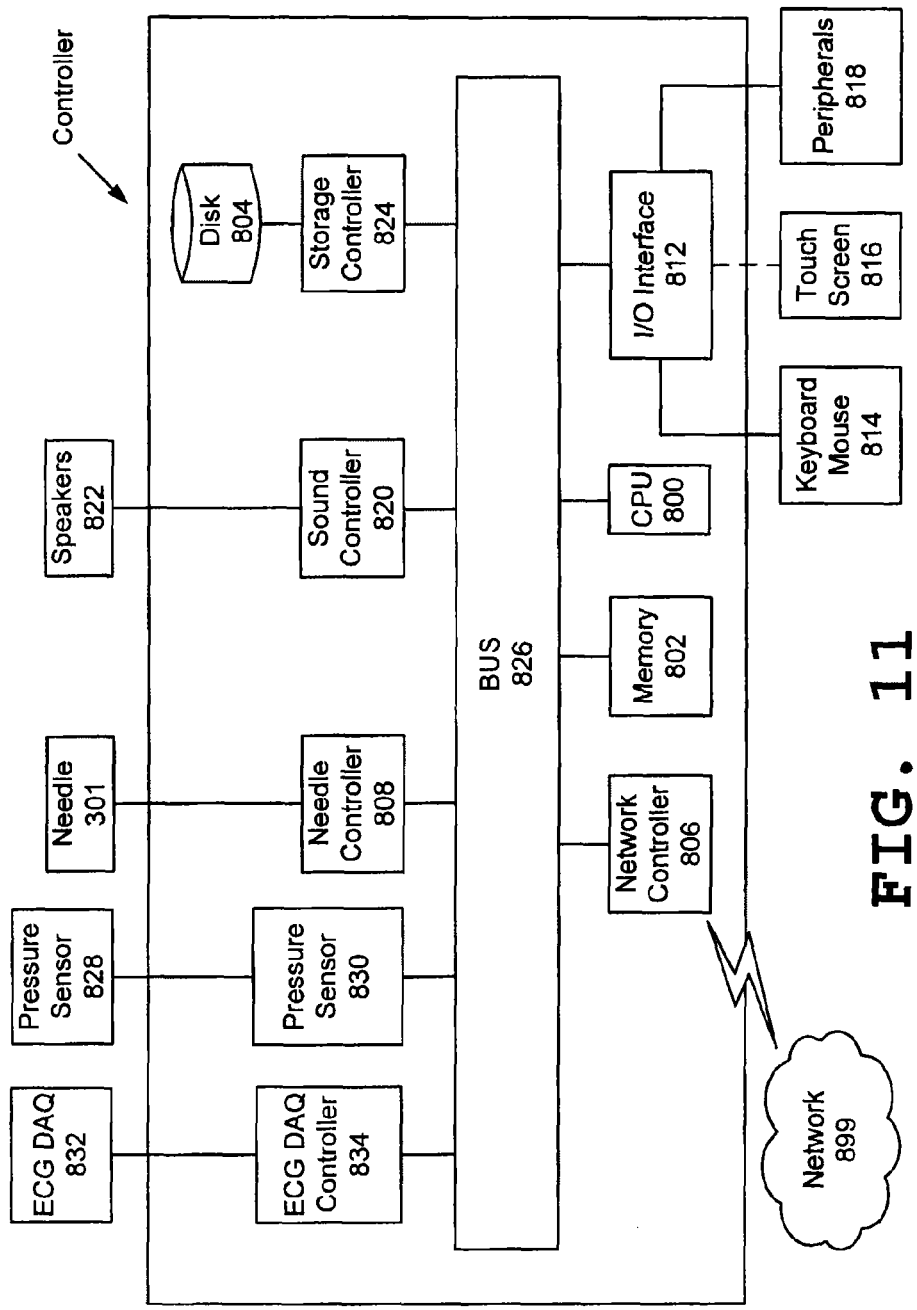
FIG. 11 is an exemplary block diagram of a controller for controlling a pericardial needle that punctures the pericardial membrane by synchronizing needle advancement with cardiac muscle motion.

FIG. 11 is a block diagram of a controller which may be used to perform the above-described processes. A hardware description of the controller according to exemplary embodiments is described with reference to FIG. 11. The pericardial needle or the needle 301 of the FIG. 11 can be any of the different embodiments of the pericardial needles as disclosed in this application.

In FIG. 11, the controller includes a CPU 800 which may be used to perform the processes described in the present disclosure. The process data and instructions corresponding to the processes described in the present disclosure may be stored in memory 802. These processes and instructions may also be stored on a storage medium disk 804 such as a hard drive (HDD) or portable storage medium or may be stored remotely.

Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the controller communicates, such as a server or computer.

Further, the claimed advancements may be provided as a utility application, background daemon, or component of an operating system, or combination thereof, executing in conjunction with CPU 800 and an operating system such as Microsoft Windows 7, UNIX, Solaris, LINUX, Apple MAC-OS and other systems known to those skilled in the art.

CPU 800 may be a Xenon or Core processor from Intel of America or an Opteron processor from AMD of America, or may be other processor types that would be recognized by one of ordinary skill in the art. Alternatively, the CPU 800 may be implemented on an FPGA, ASIC, PLD or using discrete logic circuits, as one of ordinary skill in the art would recognize. Further, CPU 800 may be implemented as multiple processors cooperatively working in parallel to perform the instructions of the inventive processes described in the present disclosure.

The controller in FIG. 11 also includes a network controller 806, such as an Intel Ethernet PRO network interface card from Intel Corporation of America, for interfacing with network 899. As can be appreciated, the network 899 can be a public network, such as the Internet, or a private network such as an LAN or WAN network, or any combination thereof and can also include PSTN or ISDN sub-networks. The network 899 can also be wired, such as an Ethernet network, or can be wireless such as a cellular network including EDGE, 3G and 4G wireless cellular systems. The wireless network can also be WiFi, Bluetooth, or any other wireless form of communication that is known.

The controller further includes a display controller 808, such as a NVIDIA GeForce GTX or Quadro graphics adaptor from NVIDIA Corporation of America for interfacing with display 810, such as a Hewlett Packard HPL2445w LCD monitor. A general purpose I/O interface 812 interfaces with a keyboard and/or mouse 814 as well as a touch screen panel 816 on or separate from display 810. General purpose I/O interface also connects to a variety of peripherals 818 including printers and scanners, such as an OfficeJet or DeskJet from Hewlett Packard.

A sound controller 820 is also provided in the controller, such as Sound Blaster X-Fi Titanium from Creative, to interface with speakers/microphone 822 thereby providing sounds and/or music. The speakers/microphone 822 can also be used to accept dictated words as commands for controlling the controller or for providing location and/or property information with respect to the target property.

The general purpose storage controller 824 connects the storage medium disk 804 with communication bus 826, which may be an ISA, EISA, VESA, PCI, or similar, for interconnecting all of the components of the controller. A description of the general features, detail features, and functionality of the display 810, keyboard and/or mouse 814, as well as the display controller 808, storage controller 824, network controller 806, sound controller 820, and general purpose I/O interface 812 is omitted herein for brevity as these features are known.

An ECG data acquisition (DAQ) controller 834 is also provided in the controller, to interface with an ECG DAQ 832, so an ECG measurement may be controlled, displayed and/or recorded via the controller, and used in a process of accessing the pericardial space 302.

A pressure sensor controller 830 is also provided in the controller, to interface with a pressure sensor 828, so a pressure measurement may be controlled, displayed and/or recorded via the controller. The pressure measurement may be used in a process of accessing the pericardial space 302.

A needle controller 808 is also provided in the controller, to interface with the needle 301, so the needle 301 may be controlled via the controller.

The disclosed methods make access into the pericardial space 302 easier and safer by utilizing the cardiac motion to puncture the parietal pericardium in synchronization with the cardiac motion.

The disclosed methods may be used to access into the pericardial space 302 in order to deliver drugs to the heart muscle and/or the coronary arteries. Since the pericardial fluid is of relatively low volume, delivering drugs via the pericardial fluid requires a relatively lower dose of drug. Additionally the disclosed methods may be used to access into the pericardial space 302 in order to introduce an agent into the pericardial space 302, thereby localizing the agent to the area around the heart muscle. Such agent is thereby contained within the pericardial fluid, without contaminating other tissue or parts. Also, due to the low turn over rate of the pericardial fluid, such agent is sustained over a longer period of time.

The disclosed methods may be used to access into the pericardial space 302 in order to insert a cathether to deliver drugs and/or agents. The disclosed methods may be used to access into the pericardial space 302 in order to insert a cathether to collect biological tissue or cells.

The disclosed methods may be used to access into the pericardial space 302 in order to insert a cathether to perform ablation of arrhythmia. A catheter is inserted into the pericardial space 302 to target a specific area of the heart. Ablation of arrhythmia is performed by directing energy through a catheter to small areas of the heart muscle that cause abnormal heart rhythm, to disconnect the source of the abnormal rhythm from the rest of the heart. This process may also be used to disconnect abnormal electrical pathways between the atria and the ventricles.

The disclosed methods may be used to access into the pericardial space 302 in order to insert a cathether or tool to ligate the left atrial appendege. The disclosed methods may be used to access into the pericardial space 302, in order to introduce implantable defibrillator and/or pacemaker electrodes into the pericardial space 302.

Figure 12A:
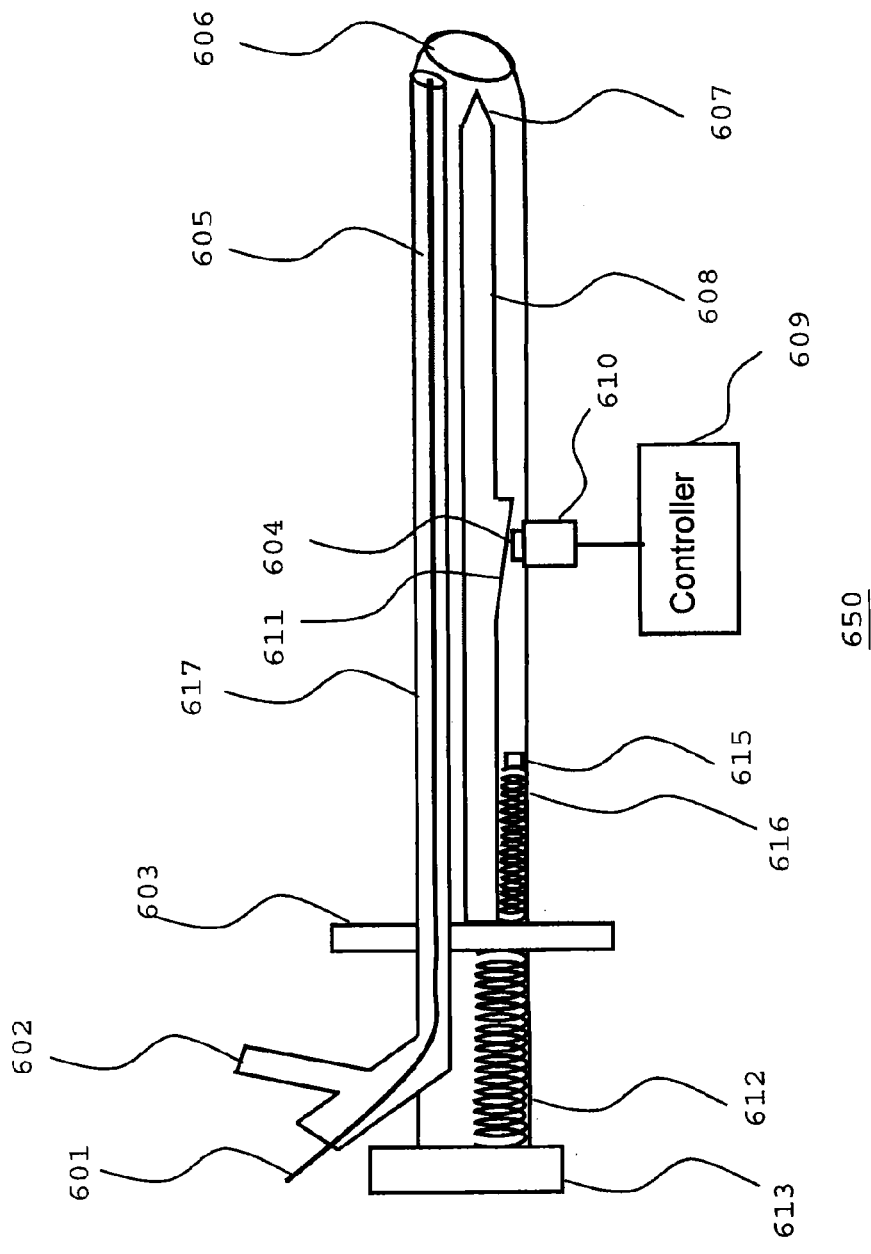
FIG. 12A is an exemplary cross-sectional illustrative view of a pericardial needle that punctures the pericardial membrane by synchronizing needle advancement with cardiac muscle motion in a baseline position.
Figure 12B:
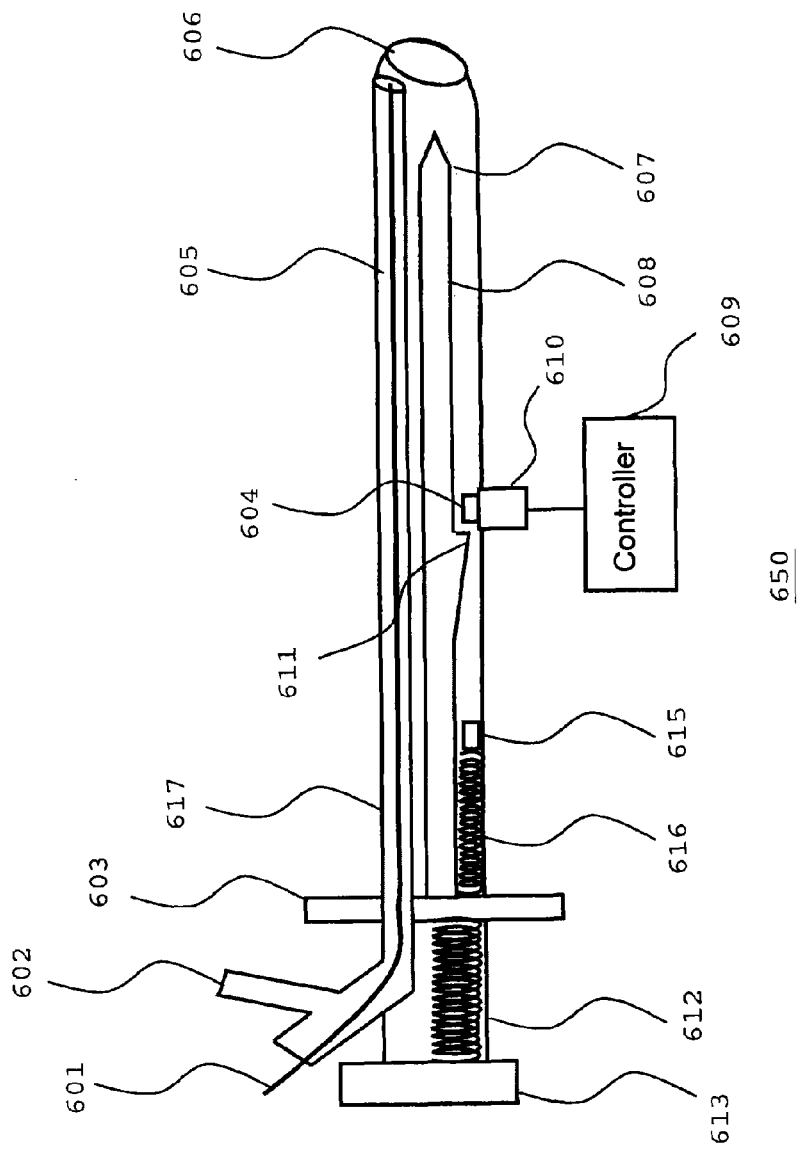
FIG. 12B is an exemplary cross-sectional illustrative view of a pericardial needle that punctures the pericardial membrane by synchronizing needle advancement with cardiac muscle motion in a retracted position.
Figure 13:
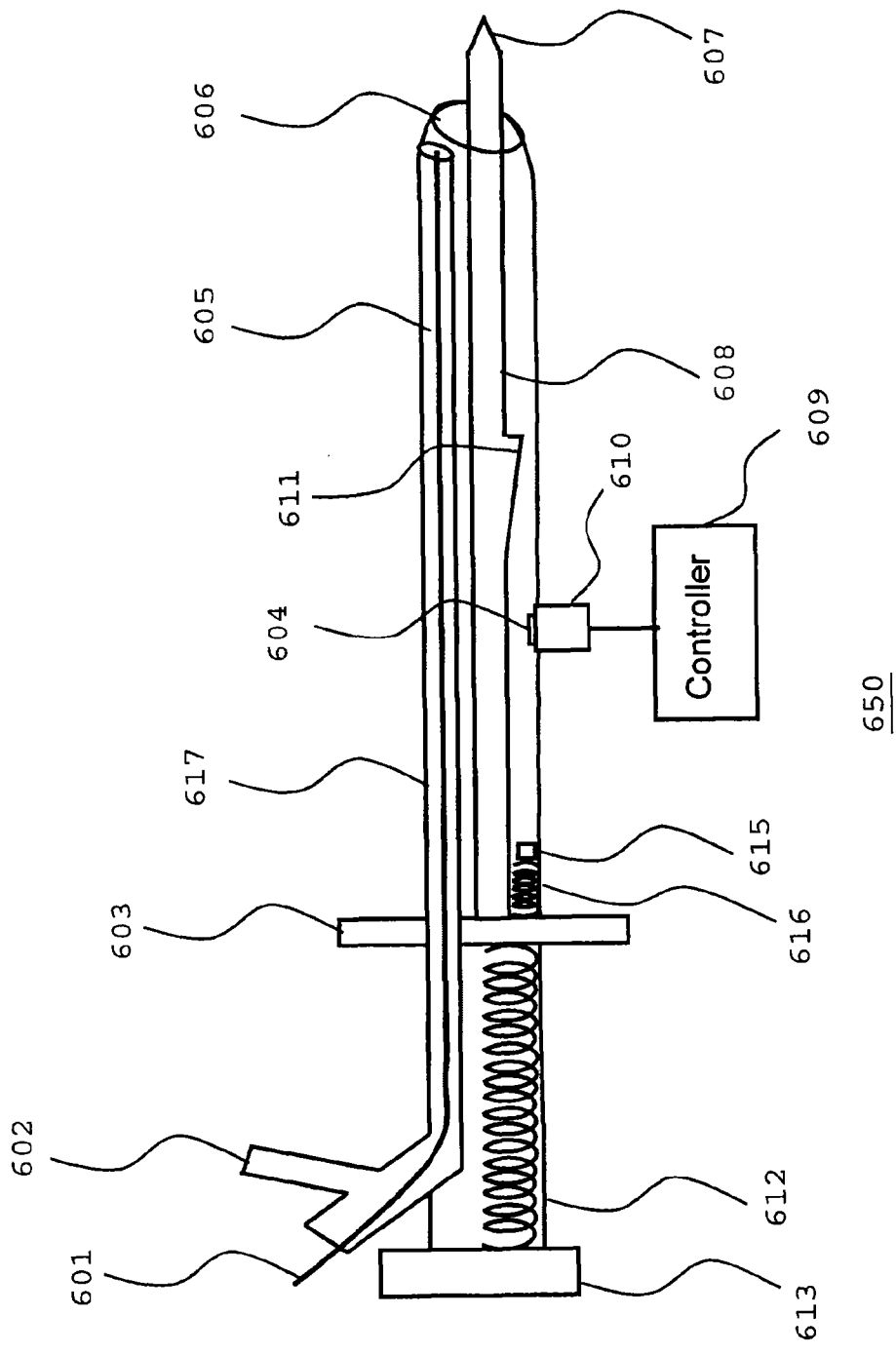
FIG. 13 is an exemplary cross-sectional illustrative view of a pericardial needle that punctures the pericardial membrane by synchronizing needle advancement with cardiac muscle motion in an extended position.

FIGS. 12A, 12B and 13 are exemplary cross-sectional illustrative views of a pericardial needle 650 that punctures the pericardial membrane by synchronizing needle advancement with cardiac muscle motion in a retracted position and an extended position, respectively.

The pericardial needle 650 has an outer needle 617 with a blunt tip 606. A lumen 605 having a wire 601, which passes through the lumen 605, is positioned inside the outer needle 617. The lumen 605 allows for contrast injection and advancing the wire 601 into the tissue once access is attained. An inner needle 608 (or the puncture needle) with a sharp tip 607 is positioned inside the outer needle 617. The inner needle 608 has an inner needle handle 603 and inner needle pin 611. The inner needle pin 611 can be engaged with a latch 604 of a lock 610 such that the lock 610 controls the latch 604. The lock 604 can be electrically, magnetically, or electromagnetically controlled by a controller 609 (as disclosed earlier in the present disclosure). When the inner needle pin 611 is engaged with the latch 604, the inner needle 608 is locked in the retracted position and the sharp tip 607 of the inner needle 608 is covered by the blunt tip 606 of the outer needle 617.

The sharp tip 607 of the inner needle 608 punctures through tissue. The pericardial needle 650 can be held like a syringe, where the middle and index fingers pull the inner needle handle 603 back, compressing a first spring 612, until the pericardial needle 650 is placed in the locked position, which is the retracted position where the inner needle pin 611 is engaged with the latch 604 of the lock 610 (FIG. 12B). The lock 610 may be an electromagnetic lock, a mechanical lock that is controlled with the controller 609. The first spring 612 is positioned between the inner needle handle 603 and the outer needle base 613 as illustrated in FIGS. 12A, 12B and 13. When in the retracted position, the first spring 612 is compressed, forcing the inner needle 608 to the extended position. The needle may be in an intermediate or baseline position in which the needle is not fully retracted and the lock 610 is not engaged (FIG. 12A). The baseline position FIG. 12A may act as the position of the needle as it is first positioned for puncturing a pericardial membrane. An operator activates the needle from its baseline position FIG. 12A to the retracted position FIG. 12B by placing retractive pressure on needle handle 603 and counter pressure on the outer needle base 613 until the needle is fully retracted and/or the needle pin 611 passes the latch 604.

The lock 610 may actuate/retract/extend the latch 604 using a spring mechanism that is placed inside the lock 610. The lock 610 may be connected to the controller 609 that controls the lock 610. Alternatively, the lock 610 may be connected to an external electrical source to supply an electrical pulse for activation that is synchronized with the motion of the heart. In particular, the lock 610 may be synchronized with the systolic motion of the heart.

When the lock 610 is activated, the lock 610 (via for example an electromagnetic mechanism) pulls the latch 604 back to disengage the latch 604 from the inner needle pin 611, resulting the inner needle 608 being released. When the inner needle 608 is released, the first spring 612 rapidly pushes the needle forward. The first spring 612 extends the inner needle 608 forward and places the inner needle 608 in the extended position and the inner needle 607 protrudes through the blunt tip 606 of the outer needle 617. As a result, a second spring 616 is compressed. Simultaneously, the lock 610 pushes the latch 604 up so that when the second spring 616 pulls back the inner needle 608, the inner needle pin 611 can be engaged with the latch 604. As a result, the inner needle can provide a rapid and brief puncture that can be controlled by the controller 609. For example, the puncture can be synchronized with systole.

The second spring 616 is positioned between a second spring base 615 and the inner needle handle 603. The parameters of the first spring 612 and the second spring 616, for example, spring constant and dimensions, may be adjusted so as to control the extension and retraction speed of the inner needle 608.

To puncture the skin and advance through tissue, an outer needle base 613 may be advanced forward to allow penetration and advancement of the pericardial needle 650 inside the tissue. Once in close proximity to the pericardium (under fluoroscopy guidance), the pericardial needle 650 can be used for puncturing. A contrast syringe (not shown) may be connected through an inlet 602 of the lumen 605 with test injections done after each puncture. Once the pericardium is punctured, contrast is seen filling the pericardial space. At this point, no additional punctures are done. A wire is advanced into the pericardial space.

Figure 14:
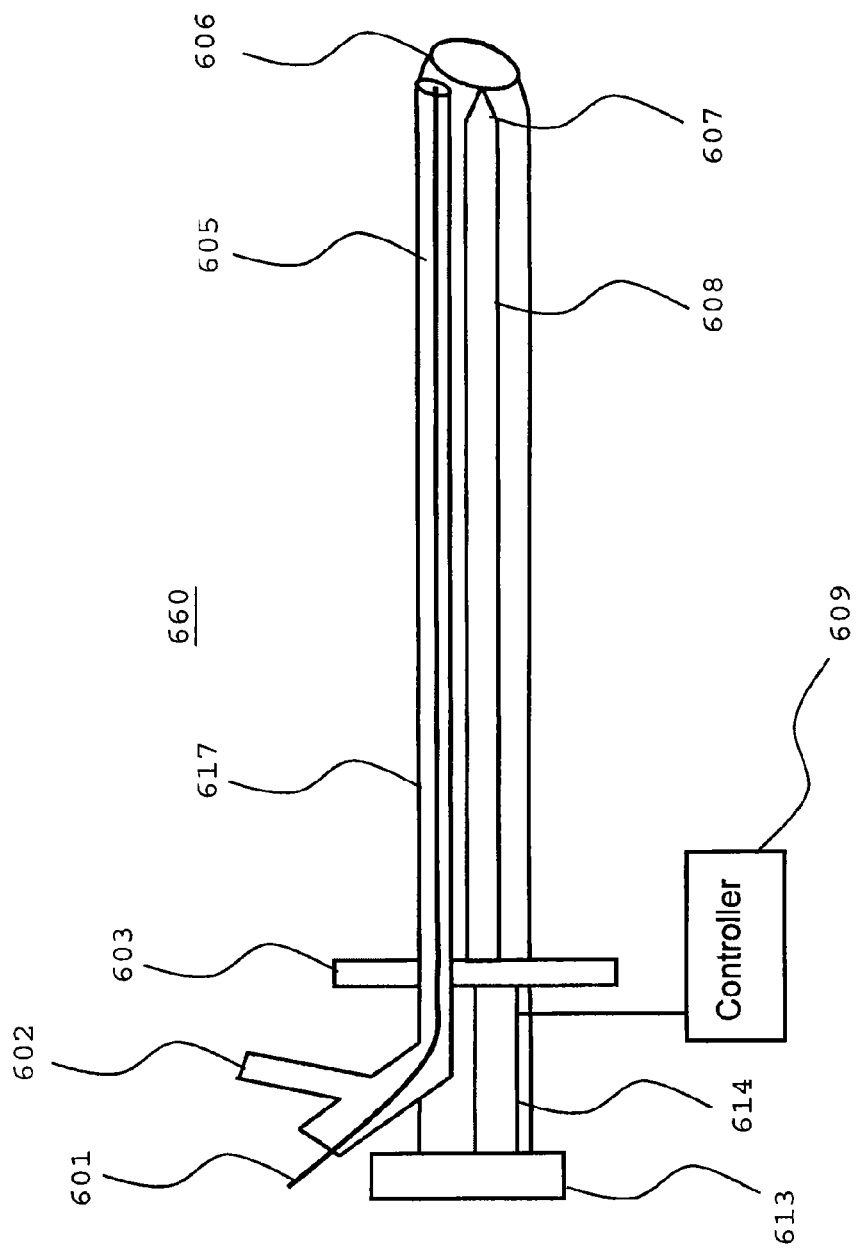
FIG. 14 is an exemplary cross-sectional illustrative view of a pericardial needle that punctures the pericardial membrane by synchronizing needle advancement with cardiac muscle motion in a retracted position.
Figure 15:
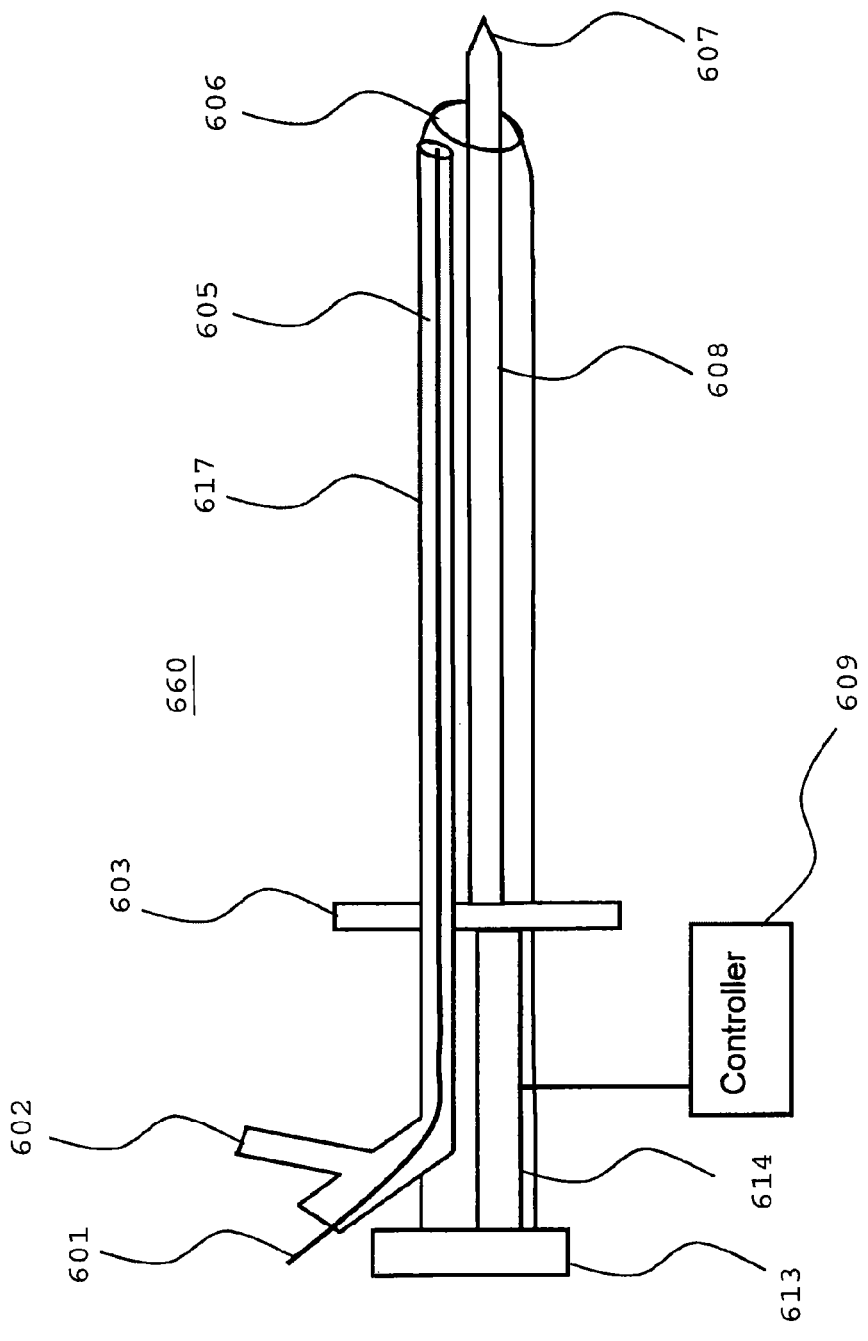
FIG. 15 is an exemplary cross-sectional illustrative view of a pericardial needle that punctures the pericardial membrane by synchronizing needle advancement with cardiac muscle motion in an extended position.

FIGS. 14 and 15 are exemplary cross-sectional illustrative views of a second embodiment of a pericardial needle 660 that punctures the pericardial membrane by synchronizing needle advancement with cardiac muscle motion in a retracted position and an extended position, respectively.

In the second embodiment of the pericardial needle 660, the first spring and the second spring is replaced with a linear actuator 614 that is controlled using the controller 609. Examples of the linear actuator 614 include, but are not limited to, piezoelectric actuators, for example, M-272 Fast Linear Pusher by PI USA, and rotary to linear motion converters. Any similar mechanism that can also generate a fast linear motion is also in the scope of this application.

The foregoing discussion discloses and describes merely exemplary embodiments. As will be understood by those skilled in the art, the present application may be embodied in other specific forms without departing from the spirit or essential characteristics thereof. Accordingly, the present disclosure is intended to be illustrative, but not limiting of the scope of the application, as well as other claims. The disclosure, including any readily discernible variants of the teachings herein, defines, in part, the scope of the foregoing claim terminology such that no inventive subject matter is dedicated to the public.

The invention claimed is:

1. A pericardial needle that produces a puncture at a heart of a human patient, the pericardial needle comprising:
    a proximal end and a distal end;
    an outer needle having a blunt tip disposed at the distal end;
    an inner needle having a sharp tip disposed at the distal end, the inner needle being disposed inside the outer needle;
    a lumen having a wire passing through the lumen and disposed on an inner surface of the outer needle;
    a handle disposed between the proximal end and the distal end, the handle being connected to the inner needle;
    a piezoelectric actuator connected to the inner needle, the piezoelectric actuator being configured to extend and retract the inner needle beyond the outer needle; and
    a controller configured to control the piezoelectric actuator;
    wherein:
    the controller is configured to synchronize the piezoelectric actuator to extend and retract the inner needle by detecting a systole phase and a diastole phase of the heart, respectively; and
    the extension of the inner needle, via the systole phase, causes the puncture of the heart.

2. The pericardial needle according to claim 1, wherein the controller receives electrocardiogram signals from an electrocardiogram of the human patient and detects the systole phase, the diastole phase, mechanical activity of the heart, and motion of the heart based on the electrocardiogram signals.

3. The pericardial needle according to claim 2, wherein the controller further monitors the electrocardiogram.

4. The pericardial needle according to claim 3, wherein the controller detects a QRS complex within the electrocardiogram, waits for a predetermined time after the controller detects QRS complex, and indicates the systole phase when the predetermined time has elapsed.

5. The pericardial needle according to claim 4, wherein the controller adjusts the predetermined time based on at least one selected from the group consisting of an age, a gender, a heart rate, a presence of an underlying heart disease, or a body mass index of the human patient.

6. The pericardial needle according to claim 5, wherein the controller detects the QRS complex within the electrocardiogram based on a slope of the electrocardiogram, and detects if the determined slope has exceeded a predetermined slope threshold.

7. The pericardial needle according to claim 6, wherein the controller adjusts the predetermined slope threshold based on at least one selected from the group consisting of an age, a gender, a heart rate, a presence of an underlying heart disease, or a body mass index of the human patient.

8. The pericardial needle according to claim 7, wherein the controller detects the QRS complex within the electrocardiogram by determining a correlation between a time window of the electrocardiogram and a predetermined QRS template, and determining if the determined correlation has exceeded a predetermined correlation threshold.

9. The pericardial needle according to claim 1, wherein the extension of the inner needle, via only the systole phase, causes the puncture of the heart.

* * * * *